United States Patent
Sullivan et al.

(10) Patent No.: US 6,212,429 B1
(45) Date of Patent: Apr. 3, 2001

(54) METHOD AND APPARATUS FOR CONVERTING A MONOPHASIC DEFIBRILLATOR TO A BIPHASIC DEFIBRILLATOR

(75) Inventors: Joseph L. Sullivan; Lawrence A. Borschowa; Richard C. Nova, all of Kirkland, WA (US)

(73) Assignee: Physio-Control Manufacturing Corporation, Redmond, WA (US)

( * ) Notice: Subject to any disclaimer, the term of this patent is extended or adjusted under 35 U.S.C. 154(b) by 0 days.

(21) Appl. No.: 09/170,923

(22) Filed: Oct. 13, 1998

(51) Int. Cl.$^7$ ...................................................... A61N 1/39
(52) U.S. Cl. .................................................................. 607/5
(58) Field of Search ................................................ 607/5, 7

(56) References Cited

U.S. PATENT DOCUMENTS

| | | |
|---|---|---|
| 4,850,357 | 7/1989 | Bach, Jr. . |
| 4,998,531 | 3/1991 | Bocchi et al. . |
| 5,044,367 | 9/1991 | Endres et al. . |
| 5,163,427 | 11/1992 | Keimel . |
| 5,199,429 | 4/1993 | Kroll et al. . |
| 5,237,989 | 8/1993 | Morgan et al. . |
| 5,265,588 * | 11/1993 | Nelson et al. ............................ 607/5 |
| 5,352,239 | 10/1994 | Pless . |
| 5,447,521 | 9/1995 | Anderson et al. . |
| 5,507,781 | 4/1996 | Kroll et al. . |
| 5,534,015 | 7/1996 | Kroll et al. . |
| 5,593,427 | 1/1997 | Gliner et al. . |
| 5,601,612 | 2/1997 | Gliner et al. . |
| 5,607,454 | 3/1997 | Cameron et al. . |
| 5,620,465 | 4/1997 | Olson et al. . |
| 5,620,470 | 4/1997 | Gliner et al. . |
| 5,634,938 * | 6/1997 | Swanson et al. ......................... 607/5 |
| 5,906,633 * | 5/1999 | Mouchawar et al. .................... 607/5 |

\* cited by examiner

Primary Examiner—George R. Evanisko
(74) Attorney, Agent, or Firm—Christensen O'Connor Johnson & Kindness PLLC

(57) ABSTRACT

An upgrade kit and method for converting a typical monophasic defibrillator into a biphasic defibrillator is provided. The upgrade kit is easily connected to a typical monophasic defibrillator and uses control signals that are commonly available in most monophasic defibrillators. Such control signals include the signals for transferring the defibrillation pulse to the patient, and for dumping unwanted energy from the energy storage capacitor. In addition, the upgrade kit avoids the need for information as to the charge level of the storage capacitor by using a discharge method that allows the production of proper biphasic defibrillation pulses regardless of the initial energy settings of the storage capacitor. More specifically, the upgrade kit determines the desired length of the biphasic defibrillation pulses according to two measurements which are taken during the defibrillation pulse. These two measurements are converted to an index referenced in a look-up table to determine the desired lengths of the two phases of the biphasic defibrillation pulse.

14 Claims, 6 Drawing Sheets

METHOD AND APPARATUS FOR CONVERTING A MONOPHASIC DEFIBRILLATOR TO A BIPHASIC DEFIBRILLATOR

FIELD OF THE INVENTION

This invention relates to defibrillators and, more particularly, to converting a monophasic defibrillator to a defibrillator capable of applying a biphasic defibrillation pulse to a patient.

BACKGROUND OF THE INVENTION

One of the most common and life-threatening medical conditions is ventricular fibrillation, a condition where the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. The switching mechanism used in most contemporary external defibrillators is a high-energy transfer relay. A discharge control signal causes the relay to complete an electrical circuit between the storage capacitor and a wave shaping circuit whose output is connected to the electrodes attached to the patient.

The relay used in contemporary external defibrillators has traditionally allowed a monophasic waveform to be applied to the patient. A typical monophasic defibrillator is shown in FIG. 1. As illustrated in FIG. 1, a host control circuit 10 activates a capacitor-charging circuit 12 to charge a storage capacitor C1 up to a high voltage level. Once capacitor C1 is charged, the defibrillator is ready to apply a defibrillation pulse. To apply a defibrillation pulse, the host control circuit 10 activates control line XFER, which closes relay switches SW1 and SW2. Relay switches SW1 and SW2 may be mechanical relays or solid state switching devices, and in some cases may be replaced by a single relay switch, such as switch SW1. Once relay switches SW1 and SW2 are closed, a monophasic defibrillation pulse travels from the capacitor C1 to the patient 14. The path of the pulse energy is from the positive terminal of the capacitor C1 to a line 20 and through switch SW1. Next, the pulse passes through a line 30 and through the patient 14 in the direction of arrow 16. Finally, the pulse passes through a line 32, switch SW2, and another line 22 to the negative terminal of the capacitor C1.

Once the storage capacitor C1 is charged, if the operator decides not to apply a defibrillation pulse to the patient, the capacitor is then discharged by the control signal DUMP. The control signal DUMP may also be activated by a "time-out" period, or when the power to the defibrillator is turned off, or by other selected events. To discharge the capacitor C1, the host control circuit 10 activates the control signal DUMP so as to close the switch SW3 and short out the remaining energy from the capacitor C1 through switch SW3 and a dump resistor R1. Dump resistor R1 limits the current from the capacitor C1 through the switch SW3 so as to prevent damage to the circuit components by discharging capacitor C1 relatively slowly.

While contemporary external defibrillators such as those described above have traditionally applied a monophasic waveform to a patient, it has recently been discovered that there may be certain advantages to applying a biphasic rather than a monophasic waveform to the patient. For example, preliminary research indicates that a biphasic waveform may limit the resulting heart trauma associated with the defibrillation pulse.

While defibrillators applying biphasic waveforms may have certain advantages, the cost of upgrading from monophasic to biphasic defibrillators can be significant. Consumers and manufacturers who have made substantial investments in the purchase and development of conventional monophasic defibrillators are faced with the costly expense of purchasing or developing entirely new biphasic defibrillators if they wish to upgrade to biphasic technology.

The present invention is directed to providing an apparatus that overcomes the foregoing and other disadvantages. More specifically, the present invention is directed to an upgrade kit for converting a conventional monophasic defibrillator into a defibrillator that is capable of applying a high-energy, biphasic defibrillation pulse to a patient.

SUMMARY OF THE INVENTION

In accordance with this invention, a defibrillator that applies monophasic defibrillation pulses to a patient may be converted into a defibrillator capable of providing biphasic defibrillation pulses. This conversion is significantly less expensive than the purchase or development of an entirely new biphasic defibrillator and reduces the training required for those who are already familiar with the controls for operating the monophasic defibrillator.

In accordance with further aspects of this invention, the upgrade kit is easily connected to and at least partially controlled by the control circuit of the monophasic defibrillator. The upgrade kit connects to easily accessible circuit components such as the terminals of the storage capacitor. In addition, an upgrade control circuit of the upgrade kit uses some of the control signals that are commonly available in most monophasic defibrillator control circuits. More specifically, the control signals for performing functions such as activating the monophasic pulse, and for dumping unwanted stored energy, may be used. These signals are commonly available in most monophasic defibrillator control circuits and are carried by control lines that can be easily coupled to and implemented by the upgrade kit. For the defibrillation pulse control signal, the upgrade kit is able to compensate for any delay time in the relay switches of the original defibrillator by delaying the activation of the faster upgrade kit switches until the slower relay switches have had time to close.

In accordance with further aspects of this invention, the upgrade kit uses a discharge method that will allow it to apply a proper biphasic defibrillation pulse regardless of the initial energy settings of the host defibrillator. The upgrade kit accomplishes this by using two measurements that are taken near the beginning of the biphasic defibrillator pulse and using the ratio of the two measurements to determine the desired length of the biphasic pulse. The desired length of the biphasic pulse may be determined by a look-up table in the upgrade control circuit. Use of this method allows the upgrade kit to apply a proper biphasic defibrillation pulse without needing information regarding the energy level to which the storage capacitor has been charged. This eliminates the need for a serial interface between the host control circuit in regard to the selection of energy levels to which the storage capacitor may be charged.

As will be readily appreciated from the foregoing description, the upgrade kit of the present invention is easily inserted into a conventional monophasic defibrillator. By using control signals that are readily available, and by not requiring a serial interface between the host and upgrade kit control circuits, the installation of the upgrade kit is simplified. The resulting upgraded defibrillator is less costly than a new biphasic defibrillator but is capable of providing the advantageous biphasic defibrillation pulses to a patient.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
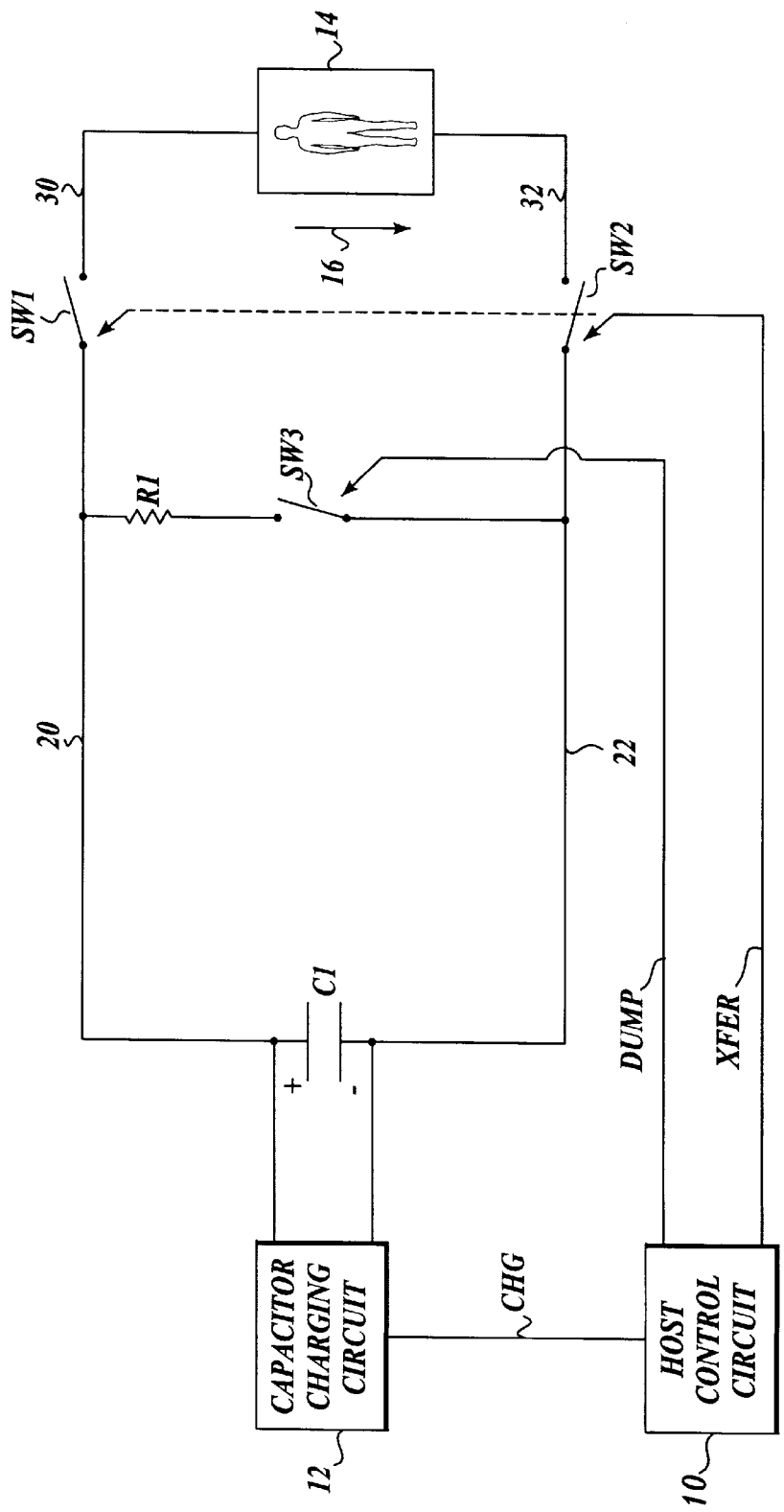
FIG. 1 is a schematic diagram of a prior art monophasic defibrillator.
Figure 2:
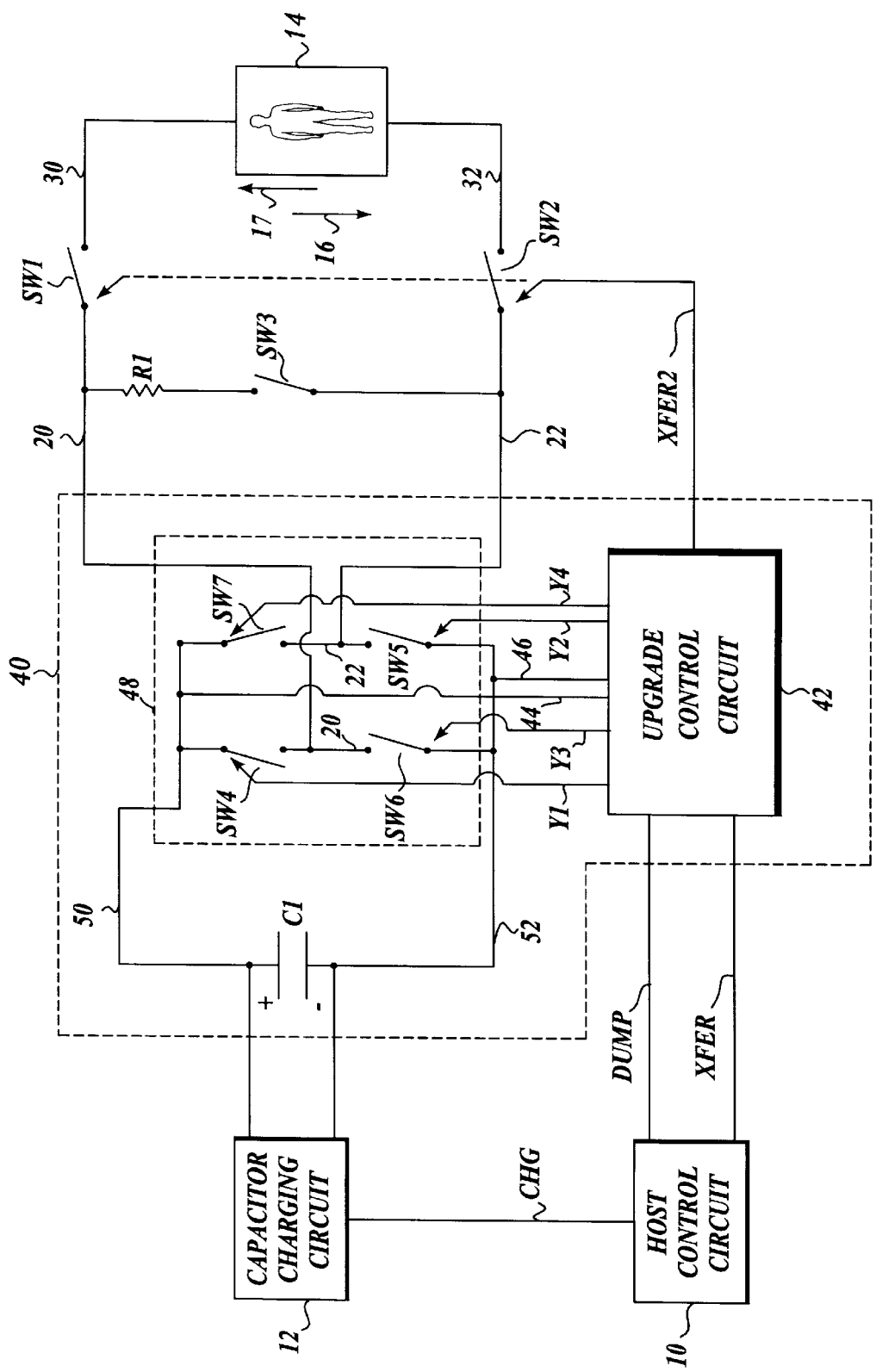
FIG. 2 is a schematic diagram of a monophasic defibrillator upgraded to a biphasic defibrillator with an upgrade kit formed in accordance with the present invention.

FIG. 2 illustrates a typical monophasic defibrillator, such as the one shown in FIG. 1, as modified by an upgrade kit 40 of the present invention to be a biphasic defibrillator. As shown in FIG. 2, the upgrade kit 40 includes a bridging circuit 48 consisting of four switches SW4, SW5, SW6, and SW7, two lines 50 and 52, an upgrade control circuit 42, and a capacitor C1'. The bridging circuit 48, consisting of the four switches SW4, SW5, SW6 and SW7, and lines 50 and 52, is coupled between a capacitor C1' and the lines 20 and 22. The two measurement lines 44 and 46 couple the upgrade control circuit 42 to the lines 50 and 52, respectively. The upgrade control circuit 42 receives as inputs the control lines DUMP and XFER from the host control circuit 10, and also the measurement lines 44 and 46. The upgrade control circuit 42 outputs control signals Y1, Y2, Y3, Y4, and XFER2. Capacitor C1' may be the same as capacitor C1, may be a new capacitor, or may be a combination of capacitor C1 and additional capacitors.

Figure 3:
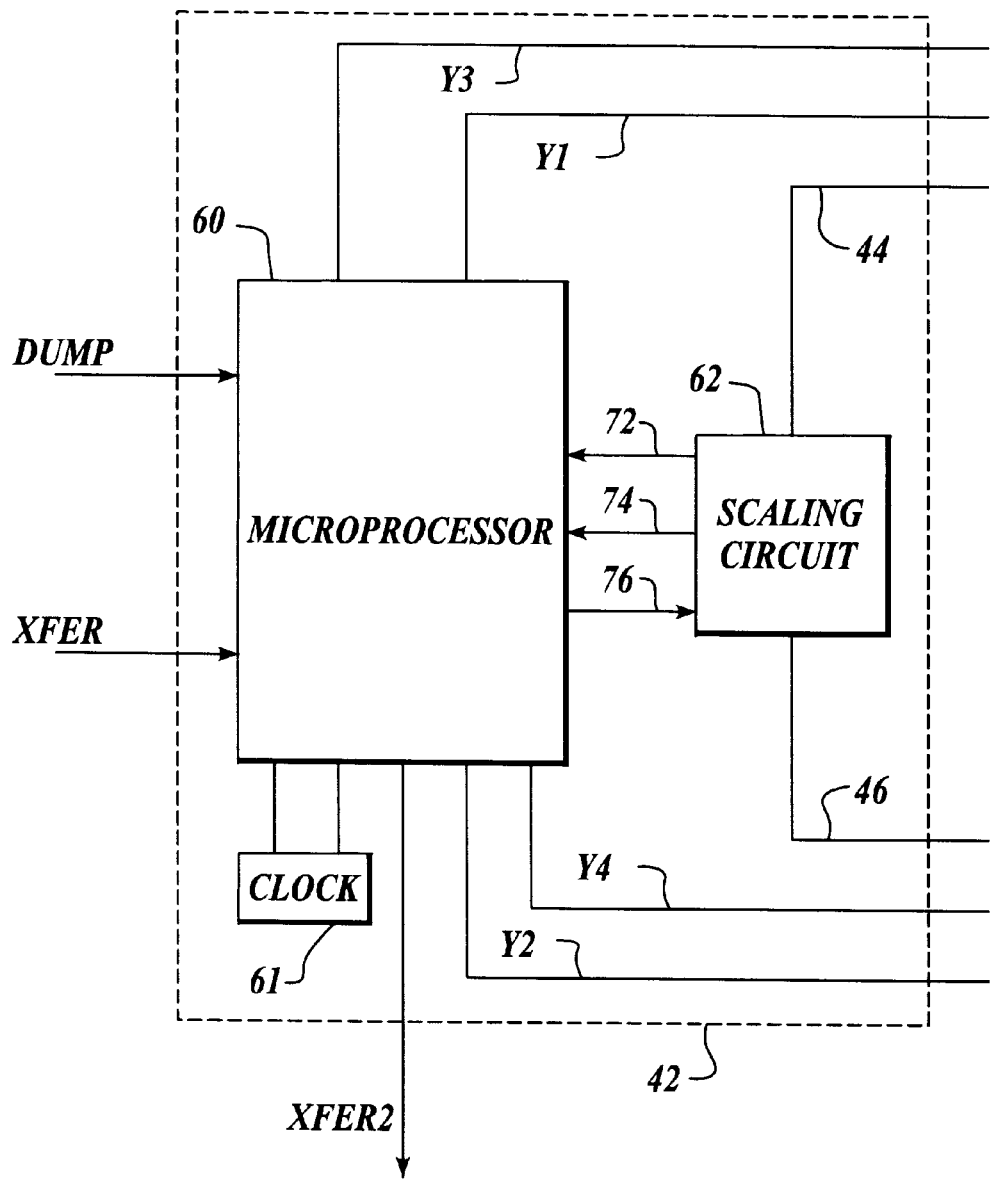
FIG. 3 is a schematic diagram of an upgrade control circuit contained in the upgrade kit shown in FIG. 2.

The upgrade control circuit 42 is depicted in greater detail in FIG. 3. A similar upgrade control circuit is described in even more detail in co-pending application Ser. No. 08/811,834, filed Mar. 5, 1997, titled "Method and Apparatus for Verifying the Integrity of an Output Circuit Before and During the Application of a Defibrillation Pulse," which is commonly assigned and incorporated herein by reference. As illustrated in FIG. 3, the upgrade control circuit 42 includes a microprocessor 60, a clock 61, and a scaling circuit 62. As will be described in more detail below, the microprocessor 60 receives the control lines DUMP and XFER from the host control circuit 10 and outputs the control signals Y1, Y2, Y3, Y4, and XFER2. The microprocessor 60 is also connected to the clock 61 and to the scaling circuit 62 by a pair of measurement lines 47 and 48, and by a control line 49. The scaling circuit 62 receives the measurement lines 44 and 46.

Figure 4:
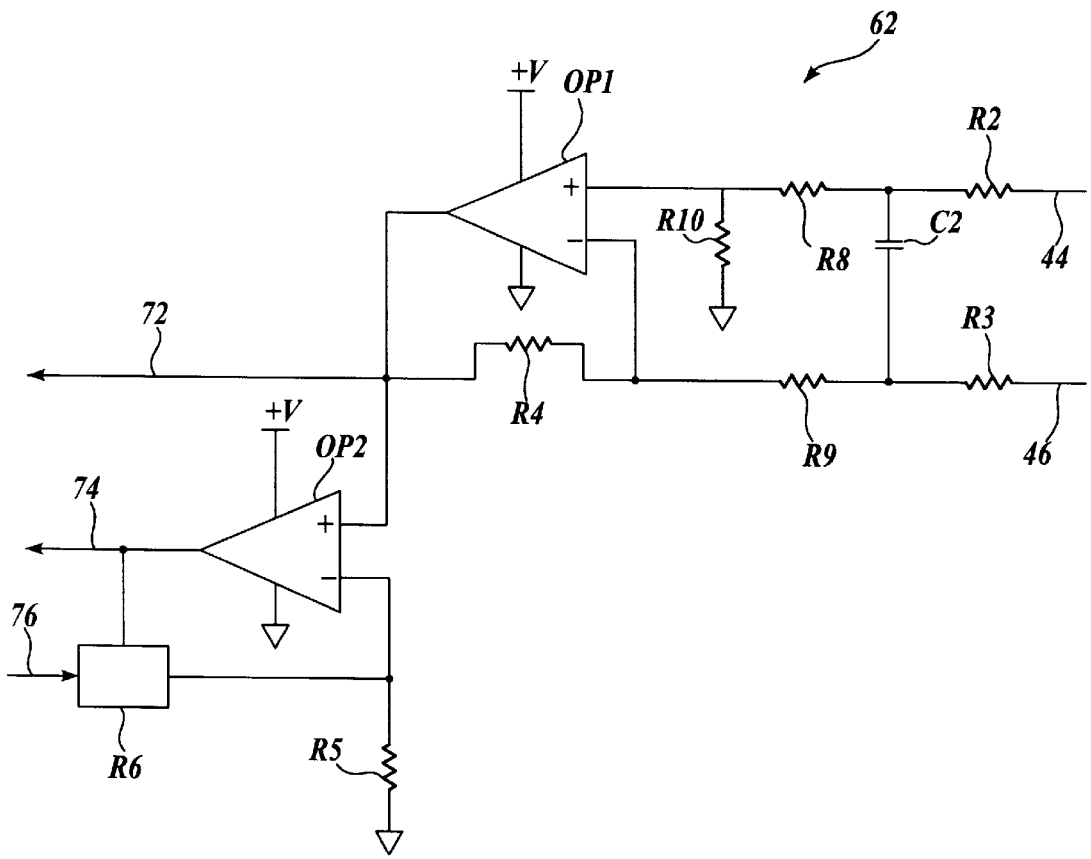
FIG. 4 is a schematic diagram of a scaling circuit component of the upgrade control circuit shown in FIG. 3.

An actual embodiment of the scaling circuit 62 is depicted in FIG. 4. The scaling circuit 62 steps down the voltage level across the energy storage capacitor C1' to a range that can be measured by the microprocessor 60 on measurement lines 72 and 74, which connect the scaling circuit 62 to the microprocessor 60. The scaling circuit 62 includes two operational amplifiers OP1 and OP2. A resistor R2 is connected in series between line 44 and another resistor R8. The other side of resistor R8 is connected to the non-inverting input of operational amplifier OP1. A resistor R3 is connected in series between the measurement line 46 and another resistor R9. The other side of resistor R9 is connected to the inverting input of operational amplifier OP1. A capacitor C2 is connected between the junction of the resistors R2 and R8 and the junction of the resistors R3 and R9. A resistor R10 is coupled between the non-inverting input of operational amplifier OP1 and ground. A resistor R4 is connected between the inverting input of operational amplifier OP1 and the output of operational amplifier OP1. The output of operational amplifier OP1 is connected to the non-inverting input of operational amplifier OP2 and to measurement line 72.

The DC voltage level of the energy storage capacitor C1' received on measurement lines 44 and 46 is stepped down for application to the operational amplifier OP1. The ratio of resistors R2 and R8 to R10 and the ratio of resistors R3 and R9 to R4 is generally very high so as to significantly step down the voltage at this stage. The values of resistors R10, R3 and R9 are also typically very high, so as to limit the current drain from the capacitor C1'. The capacitor C2 is provided to filter out high-frequency voltage spikes. In an actual embodiment of the scaling circuit 62, the scaling circuit will step down a voltage of 2,300 V across the energy storage capacitor C1' to less than 5 V on measurement line 72. In an application where the host defibrillator has a higher output voltage capability (e.g., 6,600 V) as part of the installation of the upgrade kit 40, certain minor modifications may need to be made to the capacitor charging circuit 12 so that it only charges the capacitor C1' to 2,300 V. In a preferred embodiment, the charging level of the capacitor charging circuit 12 can be altered by simply substituting internal resistor values. The microprocessor 60 is provided with a 5 V analog-to-digital converter to measure the voltage on the measurement line 72 and monitor the voltage across the energy storage capacitor C1'.

If the energy storage capacitor C1' was always charged to 2,300 V, the scaling circuit described thus far would be adequate. In the actual embodiment of the present invention described herein, however, the energy storage capacitor C1' of the host defibrillator may be charged to a range of voltage levels. The range to which the energy storage capacitor C1' may be charged in the preferred embodiment is from 100 V to 2,300 V. To detect small percentage changes in the selected voltage level of the energy storage capacitor C1', the scaling circuit is therefore adjustable to account for different voltage ranges.

To account for the range of the input voltages into the scaling circuit 62, the non-inverting input of operational amplifier OP2 is connected to the output of operational amplifier OP1. A resistor R5 is connected between the inverting input of operational amplifier OP2 and ground. A digital variable gain potentiometer R6 is connected between the inverting input of operational amplifier OP2 and the output of operational amplifier OP2. The digital variable gain potentiometer is controlled by a signal received on the control line 76 connected to the microprocessor 60. The output of operational amplifier OP2 is connected to measurement line 74. The gain provided by operational amplifier OP2 is adjustable by varying the setting of the digital variable gain potentiometer R6.

The gain of the operational amplifier OP2 is set by the microprocessor 60. A measurement is initially made of the voltage on measurement line 72 which, as described above, in the actual embodiment ranges from 0 to approximately 5 V. Based on the measured voltage, the gain of operational amplifier OP2 is adjusted to make the voltage on measurement line 74 close to 5 V. Adjusting the output to nearly 5 V allows the full range of precision of the 5 V analog-to-digital converter in the microprocessor to be used. The microprocessor 60 uses the known gain of amplifiers OP1 and OP2 in conjunction with the output voltage provided on measurement line 74 to measure the energy storage capacitor C1' voltage level. As will be described in more detail below, changes in the energy storage capacitor voltage level may be used to determine the proper pulse lengths of the biphasic defibrillation pulses, as well as for other purposes.

Returning to FIG. 2, one method for installing the bridging circuit portion of upgrade kit 40 in the monophasic defibrillator is to connect the bridging circuit 48 between the lines 20 and 22 and the capacitor C1' as illustrated in FIG. 2. It will be appreciated that lines 20 and 22 and capacitor C1 will be present in virtually any type of monophasic defibrillator. The lines 20 and 22 (as illustrated in FIG. 1) are first decoupled from the capacitor C1 and then coupled to the center portions of the bridging circuit 48 contained in the upgrade kit 40 as illustrated in FIG. 2. As described previously, capacitor C1' may be the same as capacitor C1, or may be a replacement capacitor, or may be a combination of the old capacitor C1 and additional capacitors. In a preferred embodiment where the original capacitor C1 is of a value of 30 to 50 $\mu$F, the upgrade capacitor C1' may be of a value of approximately 200 $\mu$F to accommodate the different waveform energy requirements of the biphasic circuitry. The capacitor C1' is preferably of the same physical size as the capacitor C1, so as to further simplify the upgrade process. Lines 50 and 52 from the bridging circuit 48 are then coupled to the positive and negative terminals of the capacitor C1', respectively, as illustrated in FIG. 2. In most monophasic defibrillators, the capacitor C1 and its leads are easily accessible, thus making the installation of the bridging circuit 48 in this manner a relatively simple process. The connection of the control lines DUMP, XFER, and XFER2 will be described in more detail below.

As shown in FIG. 2, the upgrade control circuit 42 receives as inputs control signals DUMP and XFER from host control circuit 10. In a typical monophasic defibrillator such as that shown in FIG. 1, control signal XFER from host control circuit 10 is used to control relay switches SW1 and SW2 so as to apply the monophasic defibrillation pulse. Such a signal is necessarily available in monophasic defibrillators because some control signal is needed to activate the relay from the storage capacitor to the patient. This makes it very easy to install the upgrade kit 40 and make it work with the host control circuit 10. More specifically, the upgrade circuit 40 is designed to use the control signal XFER to activate the upgrade control circuit 42 and apply the biphasic defibrillation pulse, as will be described in more detail below. However, as will also be described in more detail below, to use the XFER signal to activate the biphasic output circuit, the upgrade kit 40 must compensate for the relatively slow activation time of the relay switches SW1 and SW2 in some embodiments of the invention, such as when mechanical relay switches are used.

Another signal commonly found in monophasic defibrillators is the control signal DUMP as illustrated in FIG. 1. Most monophasic defibrillators have a DUMP relay such as switch SW3 for discharging energy remaining on the storage capacitor C1. Thus, the upgrade kit 40 uses the control signal DUMP from the host control circuit 10 to enable the upgrade control circuit 42 to activate control signals Y1, Y2, Y3, and Y4, which close switches SW4, SW5, SW6, and SW7, respectively, and discharge the remaining energy on the storage capacitor C1'.

The operation of the upgraded biphasic defibrillator shown in FIG. 2 is as follows. The host control circuit 10 controls the capacitor charging circuit 12 to charge the capacitor C1' to a high voltage level. When the host control circuit 10 activates control signal XFER to apply the defibrillation pulse, the upgrade control 42 takes over to create a biphasic defibrillation pulse. More specifically, for the first phase of the biphasic defibrillation pulse, the upgrade control circuit 42 activates control signal XFER2, which closes the relay switches SW1 and SW2. In an alternate embodiment, the control signal XFER2 may be actually taken directly from the control signal XFER such that the host control circuit 10 still controls the timing of the relay switches SW1 and SW2, although as described below the upgrade control circuit 42 will still need to receive the control signal XFER so as to implement the timing of the H-bridge 48 switches. After a predetermined delay (e.g., 20 milliseconds), the upgrade control circuit 42 activates control signals Y1 and Y2, which close switches SW4 and SW5. The delay is necessary to give the relatively slow relay switches SW1 and SW2 time to close before the typically faster switches SW4, SW5, SW6 and SW7 are activated. The delay timing may be implemented as part of the software programming of the microprocessor 60, and is selected based on the manufacturer's specifications for the relay switches SW1 and SW2 of the host defibrillator. The reason for the delay timing will be described in more detail below. In one actual embodiment, switch SW4 is a silicon controlled rectifier (SCR) and switch SW5 is an insulated gate bipolar transistor (IGBT), while switches SW1 and SW2 are high-energy transfer relay switches.

Once switches SW4 and SW5 are closed, the first phase of the biphasic defibrillation pulse is applied to the patient 14 in the direction as indicated by the arrow 16. This occurs as current travels from the positive terminal of capacitor C1' and, ultimately, to the negative terminal of capacitor C1'. More specifically, the current travels from the positive terminal of capacitor C1' to line 50, down through switch SW4 and to line 20. Next, the current passes through switch SW1, down line 30, through patient 14, and down to line 32. Finally, the current passes across switch SW2 to line 22, down through switch SW5 to line 52, and to the negative terminal of capacitor C1'.

As will be described in more detail below, after a specific amount of the energy from the capacitor C1' has been applied to the patient 14, upgrade control circuit 42 activates control signals Y1 and Y2 to open switches SW4 and SW5. Switches SW1 and SW2, which are controlled by control signal XFER2, remain closed. To begin the second phase of the biphasic defibrillation pulse, upgrade control circuit 42 activates control signals Y3 and Y4, which close switches SW6 and SW7, respectively. In one actual embodiment of the present invention, switches SW6 and SW7 are SCRs. While control signals Y3 and Y4 are generally illustrated as being two separate signals, in an actual embodiment they may be combined into a single control signal from the microprocessor 60.

Once switches SW6 and SW7 are closed, the second phase of the defibrillation pulse begins as current flows through the patient 14 as indicated by the arrow 17, which is opposite in direction to the current flow 16 from the first phase of the biphasic defibrillation pulse. Thus, current flows from the positive terminal of capacitor C1' to line 50, down through switch SW7 to line 22, across switch SW2 to line 32, through patient 14 to line 30, across switch SW1 to line 20, down through switch SW6 to line 52, and to the negative terminal of capacitor C1'.

As will be described in more detail below, once the upgrade control circuit 42 has determined that the second phase of the biphasic defibrillation pulse should be ended, control signals Y1 and Y2 are activated by microprocessor 60 of the upgrade control circuit 42 to close switches SW4 and SW5, and short the remaining energy on the capacitor C1' through the paths created by switches SW4 and SW6, and SW7 and SW5. The signal DUMP may be implemented by the upgrade control circuit 42 in the same way, if desired. Once the capacitor C1' is finished discharging, the upgrade control circuit 42 opens all of the switches and awaits another signal from the control line XFER from the host control circuit 10.

As described above, the control circuit 10 implements a delay between the activation of control signal XFER2 and control signals Y1 and Y2. Without the above-described delay, the H-bridge switches SW4, SW5, SW6 and SW7 would fire before the relay switches SW1 and SW2 were closed, possibly resulting in no energy delivery to the patient. The reason no energy would be delivered to the patient is because the switches SW4, SW5, SW6 and SW7 could proceed through their entire firing sequence and dump the energy from the storage capacitor C1' before the defibrillator was coupled to the patient. In other words, as described above, a biphasic defibrillation pulse is created by first activating switches SW4 and SW5, then deactivating switches SW4 and SW5, then activating switches SW6 and SW7, and then activating SW4 and SW5 so as to short out the remaining energy on the capacitor C1'. Because of the rapid nature with which this entire firing sequence occurs, the entire sequence may be accomplished before the relatively slower relay switches SW1 and SW2 have even closed. In such a case, the firing sequence of the switches SW4, SW5, SW6 and SW7 will have dumped the energy from the capacitor C1' before the defibrillator has been coupled to the patient by the relay switches SW1 and SW2. Thus, as described above, a delay must be implemented by the host control circuit 10 to ensure that relay switches SW1 and SW2 have had time to close before the firing sequence of switches SW4, SW5, SW6, and SW7 begins. In addition, it is undesirable to have the relay switches SW1 and SW2 close once the switches SW4, SW5, SW6, and SW7 have begun to fire, because the resulting large energy potential across the relay switches SW1 and SW2 could cause additional problems, such as arcing that would dissipate energy and wear out the switches SW1 and SW2.

In one embodiment of the present invention, upgrade control circuit 42 uses a discharge method that will allow it to apply a proper biphasic defibrillation pulse regardless of the initial energy settings of the host control circuit 10. The method of the present invention may be implemented as part of the software programming of the microprocessor 60. Similar methods may also be used. Certain aspects of the method of the present invention are described in more detail in co-pending application Ser. No. 09/062,192, filed Apr. 17, 1998, titled "Defibrillator Method and Apparatus," which is commonly assigned and is incorporated herein by reference. The '192 application describes the importance of the phase pulse durations in biphasic defibrillation pulses, as well as how a measured patient impedance may be used in phase timing calculations, as is done as part of the method of the present invention. Specific equations and look-up table examples are also described. Other impedance calculations and the use of look-up tables to determine phase durations are also described in U.S. Pat. No. 5,607,454, to Cameron et al., which is hereby incorporated by reference.

According to the method of the present invention, the upgrade control circuit 42 controls the timing of the two phases of the biphasic waveform according to two measurements that it takes near the beginning of the discharge. The ratio of these measurements is logarithmically related to the patient impedance, and so can be used as an index for a look-up table to determine the desired duration of the biphasic pulse. In a preferred embodiment, the measurements are voltage measurements, however, the measurements could be current measurements, charge measurements, or any other parameter that could be used to calculate impedance. In the preferred embodiment where the measurements are voltage measurements, the two measurements are taken on the measurement lines 44 and 46 which are coupled to the positive and negative terminals of the capacitor C1' through lines 50 and 52, respectively. The first measurement is made at the start of the discharge and is used to determine the initial capacitor voltage. The second measurement may be made at a fixed time interval (e.g., 4.5 ms. later). Alternatively, the second measurement may be made at an unknown time as there may be circumstances under which it would be desirable to use different intervals as long as the intervals could later be determined for the phase duration calculations.

Figure 5:
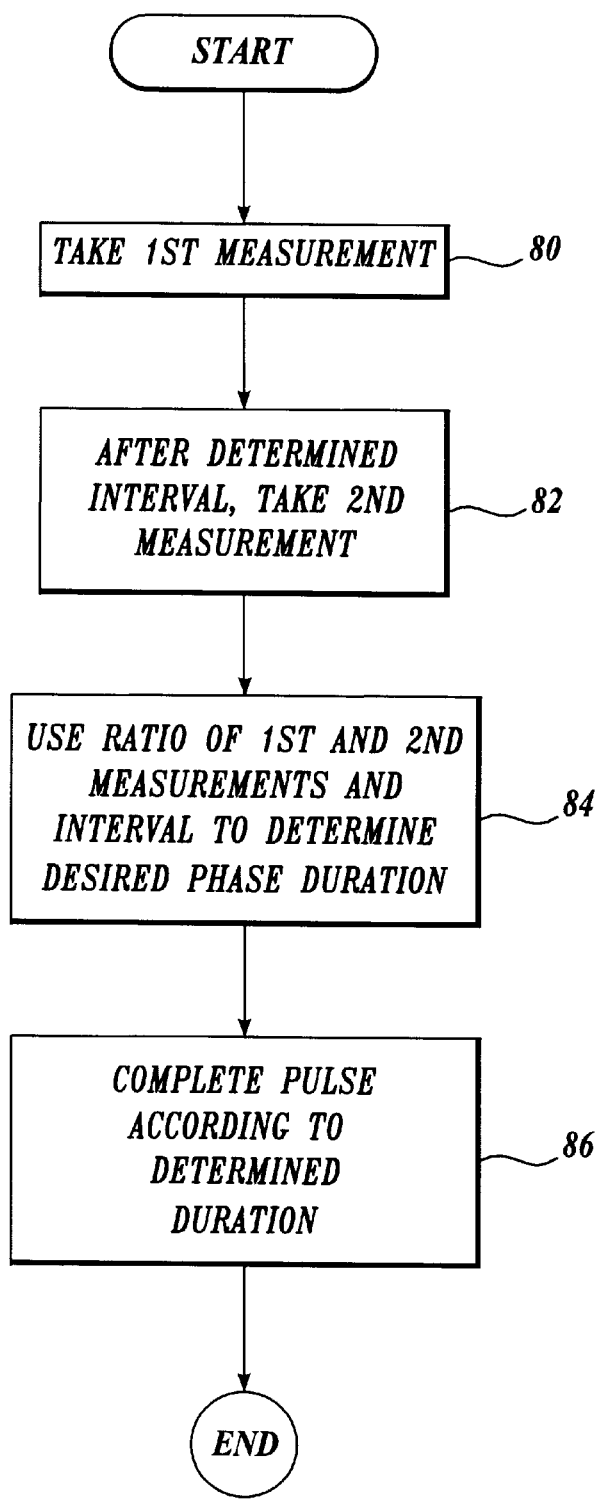
FIG. 5 is a flow diagram of a method for operating a defibrillator according to the present invention.

FIG. 5 is a flow chart illustrating the method of the present invention. The method starts when a defibrillation pulse is to be applied to a patient. At a block 80, the controller takes a first measurement. As described previously, in a preferred embodiment, the measurement is a voltage measurement taken from the energy storage capacitor through measurement lines 44 and 46. At a block 82, after a determined interval, the controller takes a second measurement. In a preferred embodiment, the determined interval may be a fixed time (e.g., 4.5 ms.), or may be at an unknown time, or otherwise based on a measured parameter such as voltage, current, or charge.

At a block 84, the controller uses the ratio of the first and second measurements, as well as the determined interval, to determine the desired phase durations. As described previously, in the preferred embodiment, the ratio of the two voltage measurements may be used as an index to reference a look-up table to determine the desired phase duration. The look-up table has predetermined phase durations that have been precalculated based on the interval, the ratios of the two measurements, and the desired ratios of energy to be delivered to the patient during the two phases. In one embodiment, the calculations of the look-up table may determine the duration of the first phase, while the second phase is a predetermined percentage of the first phase. In another embodiment, the duration of each phase is independently determined by the calculations. At a block 86, the biphasic defibrillation pulse is completed according to the determined phase durations.

Because the upgrade control circuit 42 determines the duration that the first and second phases of the biphasic pulse should last based on the ratio of the two measurements described above, its algorithm works equally well at any charge level. In other words, for a given patient, the ratio will be the same for 2 Joules as it is at 360 Joules, thus making the biphasic pulse phase durations independent of the amount of energy transferred from the storage capacitor. This is in contrast to other prior art devices, which use a control circuit with thresholds set for specific energy levels. In other words, some prior art devices determine the duration of the biphasic defibrillation pulses based on a measurement of the charge that has been delivered to the patient, or otherwise based on a single measurement of a threshold voltage or time according to a look-up table. This type of control system does not have the property of being independent of the initial charge level. In order for such a prior art "charge based" single measurement control circuit to operate at different energy levels, the control circuit needs advance information about the energy setting so that it can adjust its thresholds accordingly for controlling the durations of the biphasic defibrillation pulses.

Thus, the method used by upgrade control circuit 42 of using a ratio of two measurements allows the upgrade kit 40 to be inserted into any monophasic defibrillator, without requiring additional communication between the host control circuit 10 and the upgrade control circuit 42 regarding the energy level to which the storage capacitor C1' is being charged. This is important for an upgrade kit because it eliminates the need for a serial interface between the host control circuit 10 in regard to the selection of the energy levels to which the storage capacitor C1' may be charged. It also ensures that the phases of the biphasic pulse will be of the proper duration, regardless of any circuit or other errors affecting the charge level on the energy storage capacitor. Such measurements may similarly be used to determine the proper duration of a monophasic pulse that is being applied.

Figure 6:
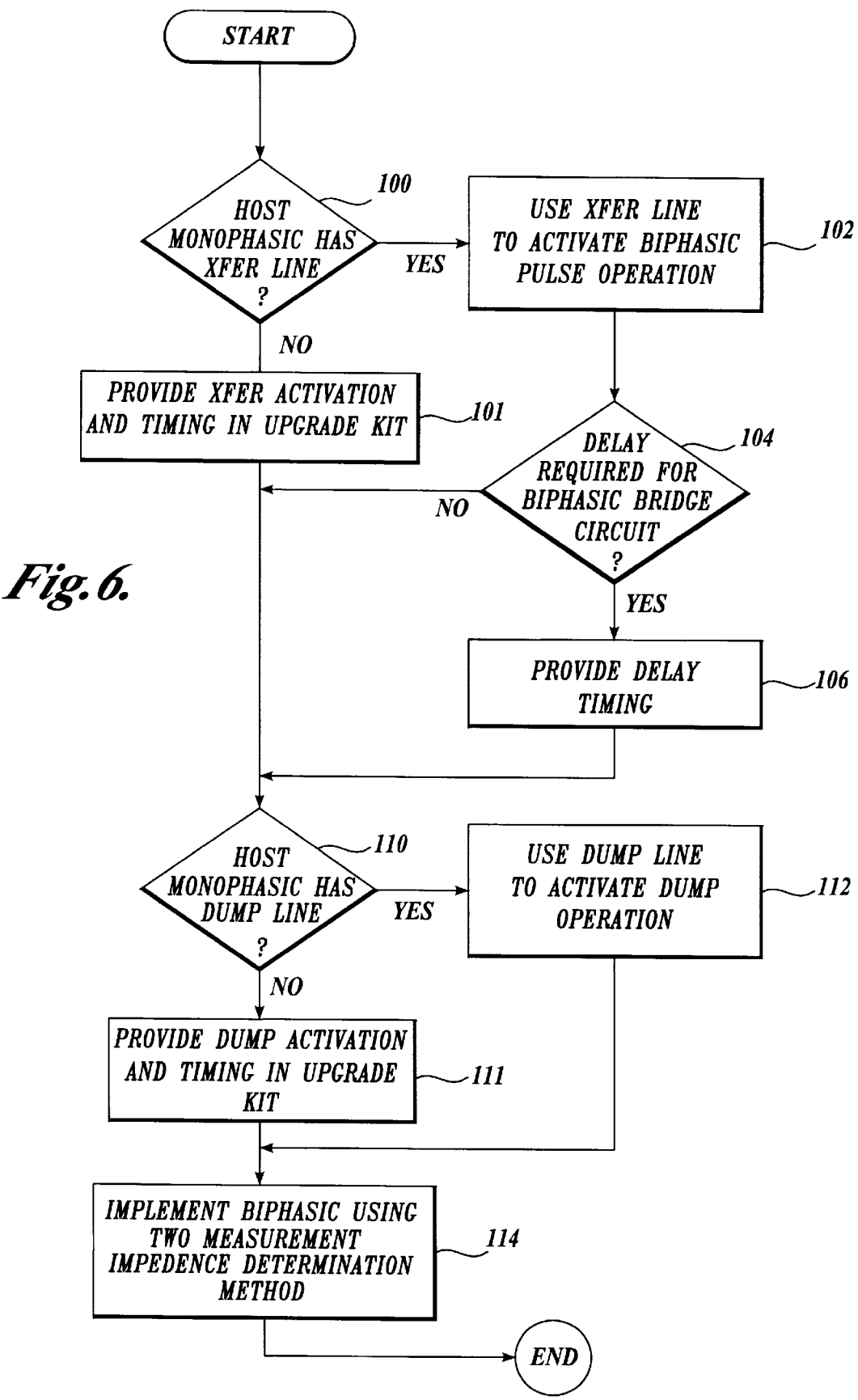
FIG. 6 is a flow diagram of a method for converting a monophasic defibrillator to a biphasic defibrillator according to the present invention.

FIG. 6 is a flow diagram illustrating the method for upgrading a monophasic defibrillator to a biphasic defibrillator according to the present invention. As illustrated in FIG. 6, at a decision block 100, a determination is made as to whether the host monophasic defibrillator has a transfer line for carrying the signal to transfer the defibrillation pulse from the energy storage capacitor to the patient. If the host monophasic defibrillator does not have a transfer line suitable for the connection to the upgrade control circuit 42, the routine continues to a block 101, and if the host monophasic defibrillator does have a suitable transfer line, the routine continues to a block 102. At block 101, a means is provided in the upgrade circuitry for activation and timing of the signal for transferring the defibrillation pulse from the energy storage capacitor to the patient.

At block 102, the transfer line from the monophasic defibrillator is coupled to the upgrade control circuit 42 and may be used to activate the biphasic defibrillation pulse operation in the upgraded defibrillator. Next, at a decision block 104, a determination is made as to whether a delay is required for the upgrade kit bridge circuit 48. As described earlier, the solid-state switches of the upgrade kit bridge circuit may be faster than the high-energy relay switches of the defibrillator such that the activation of the solid-state switches must be delayed until the relay switches have had time to close. If a delay is required, the routine continues to a block 106, and if a delay is not required, the routine continues to a decision block 110. At block 106, delay timing is provided in the upgraded defibrillator. As described previously, the delay timing is determined by the manufacturer's specifications for the relay switches SW1 and SW2 and is implemented as part of the software programming in the upgrade control circuit 42.

At decision block 110, a determination is made as to whether the host monophasic defibrillator has a DUMP line for dumping unwanted energy from the energy storage capacitor. If a DUMP line exists and its use is desired, the routine proceeds to a block 112, and if no DUMP line exists, the routine proceeds to a block 111. At block 111, a means is provided in the upgrade circuitry for activation and timing of the DUMP signal for dumping unwanted energy from the energy storage capacitor. Such means may include an external control for implementing the DUMP function. As described previously, the upgrade kit 40 is able to use the four switches of the H-bridge itself to implement the DUMP function, such that control of the old dump switch SW3 is no longer required.

At block 112, the DUMP line is coupled to the upgrade control circuit 42 which can then activate the switches of the biphasic bridge circuit and the upgraded defibrillator, so as to dump unwanted energy from the energy storage capacitor. As described above, during the dump operation, all four of the switches SW4, SW5, SW6, and SW7 may be closed during the dump operation, or else both of the switches on one side of the H-bridge, e.g., switches SW4 and SW6 or else switches SW5 and SW7, may be closed to short circuit the remaining energy from the storage capacitor C1'. The routine then continues to block 114.

At block 114, the upgraded defibrillator is implemented with the two measurement impedance determination technique that allows a proper biphasic defibrillation pulse to be applied without requiring additional serial communication between the host control circuit and the upgrade control circuit. As was described earlier, the two measurement impedance determination technique allows a proper biphasic defibrillation pulse to be produced regardless of the initial energy settings of the energy storage capacitor.

As will be readily appreciated from the foregoing description, the present invention has several advantageous features. One such feature is that since the upgrade kit bases the timing of the two phases on the ratio of two measurements, it does not require any advance information from the host control circuit in order to provide a proper biphasic discharge waveform. In addition, the upgrade kit is easily connected to the host control circuit and uses some of the control signals that are commonly available in most monophasic host control circuits. It will be appreciated that any type of monophasic defibrillator can thus be upgraded, such as monophasic truncated exponential defibrillators and Edmark defibrillators.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A biphasic upgrade circuit for converting a monophasic defibrillator into a defibrillator capable of generating a biphasic defibrillation pulse, the monophasic defibrillator including an energy storage device for providing a flow of energy, a high-energy relay that is coupled to the energy storage device and which may be activated to provide a circuit path for the flow of energy from the energy storage device, and a host control circuit that is coupled to the high-energy relay and which provides a control signal, the biphasic upgrade circuit comprising:

a bridging circuit including a plurality of controller controllable switches; and an upgrade control circuit comprising:

a controller for controlling the switches of the bridging circuit; and a means for receiving the control signal from the host control circuit of the monophasic defibrillator, the means being coupled to the controller of the upgrade control circuit, the controller having a function for activating the switches of the bridging circuit, the timing of the activation of the switches of the bridging circuit being controlled by the controller relative to the timing of the activation of the high energy relay so as to generate a biphasic defibrillation pulse.

2. The biphasic upgrade circuit of claim 1, wherein the controller of the upgrade control circuit delays the activation of the bridging circuit until the high-energy relay has had time to activate.

3. The biphasic upgrade circuit of claim 2, wherein the switches of the bridging circuit are solid-state switches.

4. The biphasic upgrade circuit of claim 1, wherein the bridging circuit is in the formation of an H-bridge.

5. The biphasic upgrade circuit of claim 1, wherein the host control circuit of the monophasic defibrillator provides a second control signal, the upgrade control circuit further comprising a second means for receiving the second control signal, the second control signal being a dump control signal for dumping unwanted energy from the energy storage device.

6. The biphasic upgrade circuit of claim 5, wherein the controller of the upgrade control circuit is coupled to the second means and includes a dump subroutine, the dump subroutine being activated when the controller of the upgrade control circuit receives the dump control signal from the host control circuit, the dump subroutine when activated causing the controller of the upgrade control circuit to close the switches of the bridging circuit so as to dump unwanted energy from the energy storage device.

7. The biphasic upgrade circuit of claim 1, wherein the upgrade control circuit provides a circuit path for a flow of energy from the energy storage device to a patient in the form of the biphasic defibrillation pulse, the biphasic defibrillation pulse having phases with lengths, the upgrade control circuit including at least one monitoring line for monitoring the flow of energy from the energy storage device to a patient, the upgrade control circuit also including a measurement subroutine for taking at least two measurements through the monitoring line that indicate the flow of energy from the storage device to the patient, the upgrade control circuit using the two measurements to determine a desired length of at least one of the phases of the biphasic defibrillation pulse.

8. A method for converting a monophasic defibrillator into a defibrillator capable of generating a biphasic defibrillation pulse, the monophasic defibrillator including an energy storage device for providing a flow of energy, a high energy relay that is coupled to the energy storage device and which may be activated to provide a circuit path for the flow of energy from the energy storage device, and a host control circuit that is coupled to the high energy relay and which provides a control signal, the method comprising:

providing a bridging circuit with a plurality of controller controllable switches;

providing an upgrade control circuit with a controller and a control signal port;

utilizing the controller to control the switches of the bridging circuit;

receiving at the control signal port the control signal from the host control circuit of the monophasic defibrillator;

the controller activating the switches of the bridging circuit; and the timing of the activation of the switches of the bridging circuit being controlled by the controller relative to the timing of the activation of the high energy relay so as to generate a biphasic defibrillation pulse.

9. The method of claim 8, wherein the activation of the switches of the bridging circuit is delayed until after the activation of the high-energy relay.

10. The method of claim 8, wherein the host control circuit of the monophasic defibrillator further generates a dump control signal, the method further comprising:

(a) receiving the dump control signal from the host control circuit at the upgrade control circuit; and (b) using the dump control signal to activate the upgrade control circuit to dump unwanted energy from the energy storage device.

11. The method of claim 10, wherein the upgrade control circuit dumps the unwanted energy by activating the switches of the bridging circuit so as to short circuit the energy storage device.

12. A method for converting a monophasic defibrillator into a defibrillator capable of generating a biphasic defibrillation pulse, the monophasic defibrillator including an energy storage device for providing a flow of energy, a high energy relay that is coupled to the energy storage device and which may be activated to provide a circuit path for the flow of energy from the energy storage device, and a host control circuit that is coupled to the high energy relay and which provides a control signal, the method comprising:

coupling a bridging circuit with a plurality of controller controllable switches into the circuit path for the flow of energy from the energy storage device;

coupling an upgrade control control circuit with a controller for controlling the switches of the bridging circuit to the host control circuit and receiving at the upgrade control circuit the control signal from the host control circuit; and activating the switches of the bridging circuit and controlling the timing of the activation of the switches of the bridging circuit relative to the timing of the activation of the high energy relay so as to generate a biphasic defibrillation pulse.

13. The method of claim 12, wherein the activation of the switches of the bridging circuit is delayed until after the activation of the high-energy relay.

14. The method of claim 12, wherein the host control circuit further generates a dump control signal, the method further comprising:

(a) receiving the dump control signal from the host control circuit at the upgrade control circuit; and (b) using the dump control signal to activate the upgrade control circuit to dump unwanted energy from the energy storage device.

* * * * *